United States Patent

Higgs et al.

Patent Number: 5,116,734
Date of Patent: May 26, 1992

[54] HIGHLY SENSITIVE METHOD FOR DETECTING PEROXIDASE

[75] Inventors: Thomas W. Higgs, Cockeysville; Floyd E. Taub, Silver Spring, both of Md.

[73] Assignee: Digene Diagnostics, Inc., Silver Spring, Md.

[21] Appl. No.: 782,918

[22] Filed: Oct. 25, 1991

Related U.S. Application Data

[63] Continuation of Ser. No. 402,448, Sep. 1, 1989, abandoned.

[51] Int. Cl.$^5$ .......................... C12Q 1/28; C12Q 1/68; C12Q 1/00; C01N 33/566
[52] U.S. Cl. ........................................... 435/28; 435/6; 435/71; 435/7.21; 436/501
[58] Field of Search .................. 435/28, 6, 7.1, 7.21, 435/501

[56] References Cited

U.S. PATENT DOCUMENTS 4,687,736  8/1987  Newman et al. ........................ 435/7

OTHER PUBLICATIONS

Adams, J. C., "Heavy Metal Intensification of DAB-Based HRD Reaction Product," J. Histochem. Cytochem 29(6), 775 (1981).

Hsu, et al., "Color Modification of Diaminobenzidine (DAB) Precipitation by Metallic Ions and its Application for Double Immunohistochemistry," J. Histochem. Cytochem 30(10), 1079–1082 (1982).

Larsson, L-I, "Immunocytochemical Detection Systems," Chap. 3, pp. 84–86, 105–108 in Immunocytochemistry: Theory and Practice, Larsson, L-I (auth), CRC Press (1988).

Primary Examiner—Christine Nucker
Assistant Examiner—M. P. Woodward
Attorney, Agent, or Firm—Kilpatrick & Cody

[57] ABSTRACT

The present invention is directed to a composition of matter and a process for detecting the presence of an oxidative catalyst in a biological sample. The composition comprises a precipitate formed by oxidation of a chromogenic substrate in the presence of the catalyst, together with two or more co-precipitated metals. A strong signal is formed with which to detect an oxidation catalyst which is localized to a target molecule. Target molecules may be nucleic acids, antibodies or cell surface antigens.

15 Claims, No Drawings

HIGHLY SENSITIVE METHOD FOR DETECTING PEROXIDASE

This is a continuation of copending application Ser. No. 07/402,448 filed on Sep. 1, 1989 now abandoned.

BACKGROUND OF THE INVENTION

The qualitative and quantitative determination of specific binding agents and of the corresponding binding partners thereof are methods used widely in the biological sciences. The methods rely on tagging or labeling either the binding agent or binding partner or both so that presence of the ligands is traceable. Examples of the above-noted agent-partner reaction are antibody-antigen, antigen-antibody, protein-protein, ligand-chelate, ligand-protein, protein-ligand, ligand-receptor, receptor-ligand, nucleic acid-complementary nucleic acid, oligopeptide-protein, protein-oligopeptide and the like.

In recent years, small size metal particles or precipitates of metal salts such as colloidal gold particles have gained popularity as markers for the localization, characterization, and quantitation of specific organic substances and structures. The detection of biological materials by metal labeling has proved useful in cytology and histology.

DESCRIPTION OF RELATED ART

Assays relying on immunologic interactions are well represented in the art. Either antibody or antigen are labeled to provide a traceable means of detection. The reactants are mixed in any of a variety of configurations to provide methods of detecting presence of and means for quantification. Representative immunoassays are disclosed in U.S. Pat. Nos. 4,486,530; 4,425,320; and 4,318,980, herein incorporated by reference.

Nucleic acid assays rely generally on the intrinsic complementary nature of single stranded nucleic acids and the conditions which favor annealing of complementary single strands into stable duplexes. The degree of complementarity need not be absolute. The methods of nucleic acid assays are well known in the art and representative assays are disclosed in U.S. Pat. Nos. 4,490,472; 4,820,630; and 4,822,731, herein incorporated by reference.

Because of the inherent difficulties of working with radiolabeled binding agents or binding partners, antibodies, nucleic acids, ligands, receptors and the like that are labeled with enzyme reporter molecules are being used more commonly in research and clinical labs. Suitable enzymes that can be employed as conjugated reporters include horseradish peroxidase (HRP), alkaline phosphatase and glucose oxidase HRP was one of the first enzymes that served as a reporter molecule and continues to find wide use and application. There are a variety of HRP substrates that in combination with peroxide can be used to discern the presence and also the location of HRP. In soluble assays suitable substrates include o-phenylenediamine, o-dianisidine, tetramethyl benzidine and 5-aminosalicylic acid. When localization of HRP is desired as in blots or in situ hybridization, substrates that produce a precipitable reaction product are selected Suitable substrates include diaminobenzidine (DAB), aminoethyl carbazol and 4-chloro-1-naphthol.

A method that does not rely on enzyme reporters is the use of colloidal metal particles (CMP) to provide visual markers. CMP's can bind proteins and thus can substitute for traditional protein dyes such as coomassie blue and amido black (see EPO 0165633A2).

A method of controlled nucleation and regulation of particle size of monodispersed colloidal gold solutions was first described by Frens, G. in *Nature Phys. Sci.* 241, 20 (1983). Several researchers have taken advantage of colloidal gold to enhance visualization of target molecules for light microscopy and also for electron microscopy.

CMP's can be attached to antibodies or avidins. A method of quantitating the different white blood cell types by labeling with a gold-labeled secondary antibody is described in U.S. Pat. No. 4,420,558 to De May et al. Leucocytes are distinguished further for the presence of endogenous peroxidase by exposing the cells to a peroxidase substrate. A method of localizing cellular antigens on a histologic section by using gold-labeled secondary antibodies is claimed in U.S. Pat. No. 4,446,238 to De May et al.

Visualization of an RNase-gold complex on a thin tissue sample can be enhanced by deposition of silver atoms on the gold particles. Danscher, G. et al., *J. Histochem Cytochem* 31, 1394 (1983). The method of Danscher et al., supra has been adapted to silver enhancement of gold-labeled streptavidin complexed to biotin-labeled cDNA. The biotinylated cDNA was used to identify neuronal cell bodies. Liesi, P. et al., *J. Histochem Cytochem* 34(7), 923 (1986).

Control of silver enhancement has been difficult where silver lactate or silver nitrate are used as sources of silver. The sensitivity of these salts to light makes development time very short and development in light impractical. Silver acetate has been shown to be advantageous because it is less sensitive to light. Development time of silver enhancement can be lengthened and development can be performed in the light by using silver acetate as the silver donor. See EP 0293947 for an alternative method of silver enhancement that minimizes the loss of silver salts to precipitation with counter ions, autocatalytic reduction to metallic silver, self-nucleation and deposition of silver on irrelevant sites. Gum arabic has been shown to further lengthen the development time. Hacker, G. et al., *J. Histotech* 11(4), 213 (1988).

SUMMARY OF THE INVENTION

The instant invention provides a method for detecting an oxidative catalyst using a combination of a chromogenic substrate and metals. The method enhances signal without the concomitant background staining associated with methods used in the art. Further, the invention provides kits comprising a plurality of the reagents used in the method. In addition, the present invention relates to a product of the above-described process, comprising a chromogenic precipitate and two or more metals, for the purpose of detecting an oxidative catalyst.

DETAILED DESCRIPTION OF THE INVENTION

The terms used herein are known to the artisan with ordinary still in the art. Nevertheless to provide a clear and consistent understanding of the specification and claims and the scope given to such terms, the following definitions are provided:

Chromogen: Enzyme substrate that yields a detectable reaction product that is usually colored.

Colloidal Metal Particle: Includes dispersions of particles, preferably sols, consisting of a metal, a metal compound or nuclei coated with a metal or metal compound. Elemental metals or ions are not included among the colloidal metal particles.

Complex: A composite of two or more compounds.

Conjugate: A molecular species composed of two or more molecules regardless of the form of attachment.

Labeling Group: A molecule which serves as a marker when attached to a biomolecule. May be a binding agent or the corresponding binding partner. May possess inherent property which makes itself readily detectable or may be attached to a reporter molecule. Thus $^{32}P$ labeled nucleic acid fragments, tritiated thymidine, HRP labeled mouse anti-rabbit Ig and biotinylated concanavalin A are examples of a labeling group.

Reporter Molecules: Synonymous with signal molecule.

Rinse: To dilute and remove substances that are not specifically bound to a sample by allowing a rinse fluid to flow over the sample or by soaking the sample in the rinse fluid. Synonymous with wash.

Signal Molecule: A compound used as a means of detection. Generally a signal molecule is attached to or reacts with a labeling group. Signal molecules may be amenable to detection by virtue of characteristics including fluorescence, radioactivity and enzymic activity. Examples of signal molecules include fluorescein and HRP.

Stabilizer: Compound that regulates the silver enhancement reaction.

The present invention is directed to a method of detecting an oxidative catalyst, to a kit for detecting an oxidative catalyst, to a kit for detecting biologic materials using peroxidase as an intermediate and to methods for detecting as oxidative catalyst.

A chromogen such as diaminobenzidine (DAB) is a commonly used oxidative substrate. For example, upon reaction with peroxidase, DAB forms an insoluble brown precipitate at the site of active peroxidase. The instant invention relates to an enhancement of the signal obtained in such a reaction. Disclosed herein is a multistep method that results in larger and thus more visible evidence of reaction at the site of an active oxidative catalyst without sacrificing specificity or causing increasing background staining. The reaction product is a signal that is darker, being black rather than beige or brown and larger, thus more visible.

Briefly a metal is added to the chromogen solution and it is believed that a chromogen-metal complex is formed upon reaction with an oxidative catalyst. Suitable oxidative catalysts include but are not limited to heme, hemoglobin, cytochromes, microperoxidase and palladium. Suitable metals include nickel, chromium and copper. The specimen containing precipitated chromogen-metal complexes at active peroxidase sites is then rinsed in a low pH solution. The specimen is exposed to a solution containing a halogenated gold salt such as tetrachlorohydroauric acid or gold trichloride and then to a solution containing a silver compound, a reducing agent and a stabilizer. A suitable silver compound is silver acetate. A suitable reducing agent is hydroquinone. A suitable stabilizer is gum arabic.

A sample suspected of containing a target such as a specific nucleic acid sequence or an antigen can be detected by hybridizing the sample nucleic acids with a nucleic acid probe or by allowing a specific antibody to react with sample tissue, cells or cell homogenate. If the sample is, for example, a histologic specimen, then it is usually frozen or embedded in paraffin. The specimen is then thin-sectioned and sections are placed on a microscope slide. The sections are treated with a labeled probe or labeled antibody and bound label is visualized either directly or indirectly.

In the case of nucleic acid probes, 10 minutes to 2 hours for probes directly labeled with HRP is allowed for a conjugate probe to hybridize to its target. Up to 62 hours may be allowed for indirectly labeled probes. A concentration of from 0.3 to 30.0 $\mu g/ml$ of probe is preferred when applying conjugate probe to a fixed sample such as a histological section.

Target nucleic acid may be detected by monitoring the presence of a labeling group attached to a nucleic acid probe. After hybridization a washing step removes any conjugate probe that is not hybridized. A labeling group is detected by reaction with the attached signal molecules or by an intrinsic detectable characteristic of said signal molecule.

A probe in which the reporter molecule relies on an oxidative reaction such as that of a peroxidase enzyme can be contacted with a chromogen to form a chromogenic precipitate which is detectable, such as by microscopic observation, at the site of the active peroxidase enzyme. In this way, an enzyme or other oxidative catalyst is detected. Chromogens that form insoluble products in the presence of an active peroxidase enzyme include but are not limited to diaminobenzidine, aminoethylcarbazole, o-toluidine, and a mixture of paraphenylene diamine and pyrocatechol.

The sensitivity of a peroxidase-linked assay can be enhanced by adding to the chromogen solution. A suitable transition metal such as nickel (Ni), copper (Cu), cobalt (Co) and chromium (Cr). The resulting chromogen-metal complex is thought to form a nucleus for further metal deposition.

A histologic section treated with hydrogen peroxide, diaminobenzidine (DAB) and nickel (Ni) in the presence of horseradish peroxidase labeled probe is then washed at low pH. Wash solution that can be used at this step include but are not limited to hydrochloric acid (HCl), phosphoric acid ($H_3PO_4$), and several buffers such as glutamic acid/HCl, citric acid/HCl, potassium phthalate/HCl, ethylene diamine tetra-acetic acid/HCl, acetic acid, sodium benzoate/HCl and potassium benzoate/HCl. The wash solution is effective at pH 5 or below. It is especially effective at pH 3 and below. A phthalic acid salt such as potassium phthalate is preferred. The section which has been "washed" with phthalate buffer is treated with one of the gold salts. The gold salts are thought to attach preferentially to the benzidine-Ni complexes.

Detection of the precipitation site may be enhanced further by depositing elemental silver onto the gold-benzidine-Ni complex. The gold treated section is contacted with a solution which contains a silver salt, a reducing agent, stabilizer and citrate buffer. The gold and nickel are thought to act as catalysts in the presence of a reducing agent to cause precipitation of elemental silver directly onto the gold-benzidine-nickel complex. Some of the silver salts that can be used are silver lactate, silver acetate, and silver nitrate. Silver acetate is preferred because it exhibits very low sensitivity to light. Silver deposition is carried out at from 0° to 20° C., and preferably from 0°-10° C. Deposition of elemental silver from silver salt is referred to in the art as development. Development using silver acetate can be performed on the stage of a light microscope or in a standard laboratory vessel such as a Coplin jar. The operator can stop the development process when in his opinion, optimum development is attained. Development can be stopped by rinsing the sample in deionized water or in photographic stop solution.

The reducing agent is any compound which reduces metal ions from solution in proximity of heavy metal. The preferred reducing agent is hydroquinone. The rate of development is directly proportional to the concentration of hydroquinone. The rate of development can be decreased by increasing the concentration of silver salt or by adding gum arabic to the enhancement solution.

The present invention provides test kits for detecting presence of peroxidase activity. By the term "kit" is meant a packaged combination of one or more vessels, containers, devices or the like holding the necessary reagents for detecting peroxidase activity. The kit is appended with written instructions for performing the method. The kit may or may not contain HRP labeled nucleic acid, antibody, ligand, antigen or the like. A suitable first kit for detecting peroxide activity comprises a plurality of vessels each containing one of the following reagents: (1) DAB; (2) DAB buffer containing heavy metal; (3) hydrogen peroxide; (4) tetrachlorohydroaurate solution; (5) low pH solution; (6) nuclear fast red stain; (7) the silver salt solution; and (8) reducing agent solution which can contain a stabilizer. A second kit for use with HRP labeled nucleic acid probes may comprise the individual reagent-containing vessels of the first kit and (9) slides; (10) protease; (11) protease buffer; (12) quenching solution; (13) denaturation buffer; (14) hybridization buffer; and (15) wash buffer. A third kit may comprise the individual reagent-containing vessels of the second kit and (16) HRP labeled nucleic acids; (17) HRP labeled nucleic acid complementary to sequences not found normally in specimens to be tested (a negative control); and (18) HRP labeled nucleic acid complementary to sequences found normally in specimens to be tested (a positive control). An example of a negative control nucleic acid is a fragment of mouse alpha satellite that does not cross-react with human or said HRP labeled nucleic acid of reagent (16) above. An example of a positive control nucleic acid is a fragment containing human Alu family repeat sequences. Bacterial plasmid sequences are an appropriate negative control for sterile specimens.

This new enhancement procedure is useful in a variety of well known procedures, such as antigen-antibody reactions, Northern blot, Southern blot, and Western blot, for detecting low levels of nucleic acid or protein target. All of these procedures readily lend themselves to methods involving an oxidative enzyme. The Examples that follow illustrate several uses for the present invention.

TABLE 1

Optimal Concentrations and Concentration Ranges of Components Used in the Silver Enhancement Procedure+

| Component | Optimal Concentration | Concentration Range |
| --- | --- | --- |
| 1) diaminobenzidine | 0.25 mg/ml | 2.5 mg/ml → 0.01 mg/ml |
| 2) hydrogen peroxide | 0.0015%* | 0.015% → 0.00005% |
| 3) nickel chloride | 0.05% | 1.0% → 0% |
| 4) Tris | 25 mM | 1M → 0.25 mM |
| 5) sodium chloride | 70 mM | 2M → 0.0M |

TABLE 1-continued

Optimal Concentrations and Concentration Ranges of Components Used in the Silver Enhancement Procedure+

| Component | Optimal Concentration | Concentration Range |
| --- | --- | --- |
| 6) potassium phthalate/HCl | 25 mM | 100 mM → 0.0M |
| 7) Tetrachlorohydroauric Acid (HAuCl$_4$) | 0.005% | 1.0% → 0.0001% |
| 8) silver acetate | 1. mg/ml | 10 mg/ml → 0.01 mg/ml |
| 9) citrate | 25 mM | 1M → 1 mM |
| 10) hydroquinone | 2.5 mg/ml | 25 mg/ml → 0.025 mg/ml |
| 11) gum arabic | 0.9% | 25% → 0.0% |

+The first five components comprise the DAB chromogen staining solution. Components 8 and 9 comprise the silver salt solution and the last two components comprise the reducing agent solution.
*All percentages are weight/volume

TABLE 2

Optimal pH and pH Ranges of Components Used in the Enhancement Procedure

| Component | Optimal pH | pH Range |
| --- | --- | --- |
| Tris | 7.6 | 10.0 → 4.0 |
| potassium phthalate/HCl | 2.2 | 5.0 → 1.0 |
| citrate | 3.8 | 5.0 → 1.0 |

TABLE 3

ENHANCEMENT PROCEDURE

The silver enhancement procedure is to be performed after the hybridization of tissue sections with HRP labeled DNA probes.

1. Stain the sections for 15 minutes with chromogen solution of diaminobenzidine.
2. Wash in 4 consecutive 1-minute deionized water washes.
3. Wash for 10 minutes in potassium phthalate.
4. Rinse in deionized water.
5. Soak for 6 minutes in HAuCl$_4$.
6. Rinse and wash in 3 consecutive 4-minute deionized water washes.
7. React for 8 minutes in an ice-cold solution consisting of silver acetate, hydroquinone, gum arabic, and citrate buffer. A solution of silver acetate in citrate buffer is mixed with a solution containing hydroquinone and gum arabic immediately before use.
8. Rinse the slides twice in deionized water.
9. Counterstain.
10. Dehydrate through graded ethanols.
11. Clear in xylene.
12. Coverslip and evaluate results.

EXAMPLE 1

In situ Hybridization

A. Hybridization

A cervical tissue sample suspected of containing human papillomavirus (HPV) is frozen-sectioned or paraffin-sectioned and sections are placed onto microscope slides. The sections are treated with protease to render the cells permeable to probe. The nucleic acids in the cell are denatured, for example by heat treatment.

An HRP labeled nucleic acid probe complementary to human papillomavirus DNA is placed in contact with the treated sections. After allowing sufficient time for hybridization to occur (from 10 minutes to 2 hours) the sections are washed to remove unhybridized probe.

It is preferred that the specimens be fixed in neutral buffered formalin and embedded in paraffin on the same day that the tissue is obtained from the patient. Optimal tissue fixation is four hours although fixation can proceed up to 24 hours. Longer fixation times may require more prolonged protease treatment.

B. Label Detection

The sections are then treated with the DAB staining solution described in Table 1, for 15 minutes. The stained sections are washed in 4 consecutive washes of deionized water. The section is then washed for 10 minutes in a post-DAB wash comprising 25 mM potassium phthalate pH 2.2. The phthalate-treated sections are washed in deionized water and exposed to a 0.005% (w/v) solution of tetrachlorohydroauric acid ($HAuCl_4$) for 6 minutes. The treated sections are washed in 3 consecutive 4-minute deionized water baths. The washed sections are treated for 8 minutes in an ice-cold silver enhancement solution of 1 mg/ml silver acetate, 2.5 mg/ml hydroquinone, 0.9% (w/v) gum arabic, and 25 mM citrate buffer pH 3.8. The treated sections are rinsed twice in deionized water, counterstained with nuclear fast red, rinsed in deionized water and dehydrated through graded ethanol solutions. The sections are then cleared in xylene, mounted and observed under a microscope. The presence of human papillomavirus is represented by black granules observed against a pink background.

EXAMPLE 2

Liquid Hybridization

DNA from HPV is isolated. The crude preparation can be purified further by techniques known in the art, e.g. PEG precipitation or phenol-chloroform extraction and alcohol precipitation or the crude prep can be used directly with application of the polymerase chain reaction. The DNA is fragmented, denatured and exposed for two hours to HRP labeled probe nucleic acid specific for human papillomavirus. The nucleic acids are then fractionated by gel electrophoresis and hybridized fragments are visualized by staining the gel with the Label Detection procedure of Example 1.

EXAMPLE 3

Filter Hybridization of DNA

Human papillomavirus DNA is isolated, purified and fragmented. The DNA fragments are sized by gel electrophoresis. DNA in the gel is transferred to a membrane filter (Southern blot) and the blot is hybridized with HRP labeled probe specific for human papillomavirus DNA. The filter is washed to remove unhybridized probe. Hybridized fragments are visualized with the Label Detection procedure of Example 1.

EXAMPLE 4

Filter Hybridization of RNA mRNA transcribed from human papillomavirus DNA is isolated and purified on an oligo-dT column. The mRNA is then fractionated on a denaturing gel and transferred to a membrane filter (Northern blot). HRP labeled probe specific for human papillomavirus DNA is reacted with the blot. The blot is washed to remove unhybridized probe. The blot is then stained by the Label Detection procedure of Example 1.

EXAMPLE 5

Immunohistochemistry and Immunocytochemistry

Fixed tissue sections (immunohistochemistry) or cell suspensions (immunocytochemistry) are placed onto slides. Monoclonal or polyclonal antibodies are applied to the slides. In this and other immunology-based examples either the primary antibody is conjugated with HRP or an appropriate HRP labeled secondary antibody can be used. In the latter case, the samples are washed profusely following the primary antibody incubation. The antibodies are prepared in a suitable buffer containing carrier protein such as bovine serum albumin, serum or gelatin. The slides are incubated in a humidified chamber for 5 minutes to overnight (about 18 hours). Following the incubation the slides are washed vigorously for five minutes in a large volume of buffer such as that used to dilute the antibody. (Another procedure is to label either the primary or secondary antibody with biotin. In that case an HRP labeled avidin or HRP labeled streptavidin is used to bind biotin.)

The slides are then exposed to the DAB/Ni solution for 15 minutes followed by 4×1 minute washes in $dH_2O$. The slides are incubated for 10 minutes in 25 mM potassium phthalate pH 2.2 and rinsed in $dH_2O$. Then the slides are incubated for 6 minutes in 0.005% (w/v) $HAuCl_4$ and washed 3×4 minutes with $dH_2O$. The next incubation is for 8 minutes in an ice-cold solution of 1 mg/ml silver acetate, 2.5 mg/ml hydroquinone, 0.9% (w/v) gum arabic and 24 mM citrate buffer pH 3.8. The slides are rinsed twice in $dH_2O$, counterstained, dehydrated through ethanol, cleared in xylene, mounted and coverslipped. A common source of a negative result is overfixation. The effects of mild overfixation may be remedied by digesting the section more extensively with protease.

EXAMPLE 6

Protein Blot

Proteins are separated through polyacrylamide gels under reducing or non-reducing conditions. Following electrophoresis, the separated proteins are transferred or blotted onto membrane supports such as nitrocellulose. The membranes are then incubated in a buffer containing carrier protein and/or detergent to prevent adventitious binding of antibodies. The membranes are then exposed to the HRP labeled monoclonal antibody for 1-24 hours, rinsed and treated as above in the Label Detection procedure of Example 1. Biotinylated antibodies and HRP labeled avidin products can be substituted for HRP labeled antibodies.

EXAMPLE 7

ELISA

[This is one of many configurations of an ELISA].

Antigen is coated onto the wells of a microtiter dish using bicarbonate buffer pH 9.6. The wells are washed profusely with a buffer containing carrier protein and/or detergent and then the antibody samples are introduced into the wells. The plates are incubated, the wells washed thoroughly and the HRP labeled antibody is charged into the wells. Following incubation, the wells are washed and subjected to the Label Detection procedure of Example 1.

EXAMPLE 8

Immunoprecipitation

Fixed amounts of HRP labeled antigen are charged into 10×75 mm test tubes and an appropriate antibody is titrated across the tubes. One tube is charged with buffer only (negative control), one tube is charged with an experimental serum sample and one tube is charged with undiluted antibody (positive control). Following an incubation period, secondary antibody conjugated to agarose beads is added to each tube, the contents mixed and allowed to incubate. The beads are separated by centrifugation, washed with buffer and exposed to the Label Detection procedure of Example 1. Reactivity of individual tube contents is assessed visually, colorimetrically, photometrically or by any method that distinguishes the degree of flocculation or turbidity.

EXAMPLE 9

Nucleic Acid Hybridization

Nucleic acid hybridization can be accomplished in agarose or polyacrylamide gels. Following electrophoretic separation, the gels are dried under vacuum at elevated temperatures or under room conditions. The dried gels are then treated as a membrane support would in the hybridization, wash and detection of bound labeled sequence procedures alluded to in the sections on filter hybridization.

EXAMPLE 10

Nucleic Acid Immunoassay

The wells of microtiter plate are coated with an antibody specific for double stranded DNA using bicarbonate buffer pH 9.6. During the coating incubation, single-stranded DNA samples are mixed with HRP labeled single stranded probe DNA in solution under conditions that favor hybridization of nucleic acids. The DNA solution is then introduced into the washed wells of the microtiter dish and the dish incubated. Then the wells are washed profusely and subjected to the Label Detection procedure of Example 1 to quantify bound duplexes.

EXAMPLE 11

In situ Hybridization

A specimen suspected of carrying human papillomavirus (HPV) is obtained from a patient. The solid tissue specimen is fixed immediately in neutral buffered formalin for four hours and embedded in paraffin. Four micron sections are cut from the paraffin blocks, floated on deionized water and placed onto microscope slides. The slides are placed into a 60° C. oven for two hours.

The sections are deparaffinized through two xylene washes of 5 minutes each and then rinsed in two changes of absolute ethanol of 3 minutes each. The slides are then immersed in a solution to quench endogenous peroxide. Said solution comprises hydrogen peroxide or sodium azide. The slides are incubated in the quenching solution for lo minutes and then passed through two changes of deionized water. The slides are then placed into a 37° C. solution containing protease and incubated for 10 minutes. Following the digestion step the slides are rinsed through two changes of deionized water and then dipped into 95% ethanol. The slides are air dried. (Ideally, the slides should be used within 20 hours.) Probe DNA's containing cloned portions of papillomavirus DNA of four different types are available for hybridization. The probes distinguish types 6, 11, 16 and 18. Probes for HPV types 6 and 11 are pooled. Probe DNA is suspended well in hybridization buffer and kept on ice. Denaturation buffer is placed onto the slide in an amount sufficient to amply cover the sections. The slides are then placed into a 100° C. environment where they are incubated for 10 minutes. Additional denaturation buffer is added when necessary. Following the denaturation step, excess buffer is removed by standing the slides on edge on a blotter without touching the specimen or by aspiration. When the slides are cool enough to handle, probe mixture sufficient to cover each section is added to the slide. The slides are incubated in a humid chamber at 37° C. for 1 hour. The slides are dipped in wash buffer at 37° C. and then transferred to a second container of wash buffer at 37° C. and incubated for 10 minutes.

Immediately before removing the slides from the wash buffer, the DAB substrate containing heavy metal is prepared in an opaque or foil-lined container. Several drops of 3% hydrogen peroxide are added to the DAB solution. The slides are placed in the DAB solution, the container is covered and the slides incubated for 15 minutes at room temperature. Color development is terminated by four 1-minute washes in deionized water.

The slides are then placed into the phthalate buffer and incubated for 10 minutes. The slides are rinsed in deionized water. The slides are then transferred to the tetrachlorohydroaurate solution and incubated for 6 minutes. The slides are rinsed through three 3-minute deionized water washes. Immediately before use, the slides are incubated in the silver-reducing agent solution for 8 minutes and the slides are rinsed through two changes of deionized water. The slides can be counterstained in nuclear fast red for 30 seconds and rinsed in distilled water.

The slides are dehydrated through an ethanol series followed by wash in 100% xylene and coverslips applied with a mounting medium. Slides can be viewed with a standard light microscope. Positive hybridization is manifest as a black granule against a light pink background.

EXAMPLE 12

Receptor Assay

Lymphocytes are prepared from whole blood and the white cells are fixed in acid alcohol (3:1 v/v of methanol and glacial acetic acid). The fixed cells are then air dried onto slides. Biotinylated lectin, for example concanavalin A, phaseolus vulgaris agglutinin or peanut agglutinin, is applied to the slide and the slides are incubated. Following incubation the slides are washed profusely in buffer and then incubated in a solution containing HRP labeled streptavidin. Following that incubation the slides are rinsed through fresh buffer and bound HRP visualized using DAB and silver enhancement as described above.

EXAMPLE 13

Diagnostic Assays

Presence of herpes simplex virus in a sample can be determined in at least four ways: immunologic assays, such as ELISA and immunocytochemistry, filter hybridization and in situ hybridization. For the immune assays, either a polyclonal or monoclonal antibody is used. The antibody may cross-react with types 1 and 2 or distinguish the two types. The method for performing an ELISA is similar to that described in Example 7. Herpes antigen can be coated onto the solid phase and used to capture anti-herpes antibody in serum samples. Bound anti-herpes antibody is detected using an HRP labeled anti-human antibody and the Label Detection procedure of Example In another approach, circulating virus can be detected by using an anti-herpes antibody attached to the solid phase. Bound virus is detected using another or the same anti-herpes antibody with the applied antibody being labeled with HRP.

Cell or tissue samples are prepared for histology. HRP labeled anti-herpes antibody is applied to the slide, the slides incubated, washed and treated using methods similar to that described in Example 5 to detect bound label.

Those same cells or tissue samples prepared for histology, with appropriate modifications, can be used for in situ hybridization according to Examples 1 and 11 using HRP labeled nucleic acid probes specific for either type 1 or type 2 or both.

Presence of herpes simplex nucleic acid in a sample may be determined by filter hybridization using the methods described in Example 3 and using HRP labeled nucleic acid probes as described above.

Other pathogens such as adenovirus and HIV, and some genetic disorders, such as those associated with specific major histocompatibility antigens or haplotypes, are amenable to detection by both immunologic means and nucleic acid means as is herpes simplex described above. On the other hand, because of assay facility or specificity, or the current state of the art, other pathogens and genetic diseases such as certain cancers, Huntington's disease and Down syndrome, may be detectable by only immunologic means or nucleic acid means. With regard to genetic diseases, it is sometimes required only to determine whether one is a carrier or not of a deleterious gene.

EXAMPLE 14

Cytology

Cells are obtained from a bronchial lavage. The cells are fixed and dried onto slides. The nucleic acids are denatured and HRP labeled single stranded nucleic acid probe complementary to cytomegalovirus nucleic acid is applied to the slide. Following incubation under conditions that favor annealing, unhybridized probe is washed away and bound probe is visualized using the Label Detection procedure of Example 1.

It will be appreciated that the methods and compositions of the present invention are capable of being incorporated in the form of a variety of embodiments, only a few of which have been illustrated and described above. The invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalence of the claims are to be embraced within the scope of the invention.

What is claimed is:

1. A process for detecting the presence of an oxidative catalyst in a sample containing a biological substance, comprising in the order recited:
   (a) treating the sample with a chromogenic substrate of the oxidative catalyst;
   (b) treating the sample with a transition metal;
   (c) washing the sample in a low pH phthalic acid solution;
   (d) treating the sample with a gold salt;
   (e) treating the sample with a silver salt in the presence of a reducing substance; and
   (f) detecting the presence or absence of a precipitate, whereby the presence of a precipitate indicates the presence of said catalyst.

2. The process of claim 1 wherein the biological substance is a nucleic acid, a protein or a cell.

3. The process of claim 1 wherein the oxidation catalyst is a peroxidase enzyme.

4. The process of claim 1 wherein the chromogenic substrate is diaminobenzidine.

5. The process of claim 1 wherein the metal is nickel, chromium, copper or cobalt.

6. The process of claim 1 wherein the silver salt is silver acetate, silver nitrate or silver lactate.

7. The process of claim 1 further comprising treating the sample with a gum in step (e).

8. The process of claim 1 wherein the low pH solution is a pH 2.2 solution of potassium phthalate.

9. A reagent kit for use in diagnostic and analytical assays comprising:
   (a) a chromogenic substrate producing a dark precipitate upon reaction with an oxidant;
   (b) an oxidant of the chromogenic substrate;
   (c) a metal forming a chromogen-metal complex upon reaction with the oxidant in the presence of an oxidative catalyst;
   (d) a halogenated gold salt,
   (e) a phthalic acid solution having a pH between 5.0 and 1.0,
   (e) a silver compound, and
   (f) a reducing agent and a stabilizer for the chromogen-metal complex-reduced precipitate.

10. The kit of claim 9 wherein the oxidation catalyst is a peroxidative catalyst.

11. The kit of claim 9 wherein the oxidation catalyst is a peroxidase enzyme.

12. The reagent kit of claim 9 wherein the chromogenic substrate is selected from the group consisting of diaminobenzidine, aminoethylcarbazole, o-toludine, and a mixture or paraphenylene diamine and pyrocatechol, the oxidant is selected from the group consisting of hydrogen peroxide and horseradish peroxidase, the metal is selected from the group consisting of nickel, chromium, cobalt and copper, the oxidative catalyst is selected from the group consisting of heme, hemoglobin, cytochromes, microperoxidase, and palladium, the halogenated gold salt is selected from the group consisting of tetrachlorohydroauric acid and gold trichloride, the silver compound is selected from the group consisting of silver, silver lactate, silver nitrate and silver acetate, the reducing agent is hydroquinone, and the stabilizer is gum arabic.

13. The reagent kit of claim 9 wherein the substrate is diaminobenzidine in a concentration between 2.5 mg/ml and 0.01 mg/ml; the oxidant is hydrogen peroxide in a concentration between 0.0015% and 0.00005%; the metal is a nickel salt in a concentration between 1.0% and greater than 0%; the gold salt is tetrachlorohydroauic acid in a concentration between 1.0% and 0.0001%; the phthalic acid solution is a Tris TM-potassium phthalate-HCl solution having respective concentrations between 1M and 0.25 mM and 100 mM and greater than 0.0M; the silver compound is silver acetate in a concentration between 10 mg/ml and 0.01 mg/ml; and the reducing agent is hydroquinone in a concentration between 25 mg/ml and 0.025 mg/ml.

14. The kit of claim 9, further comprising:
(a) horseradish peroxidase (HRP) labeled nucleic acids;
(b) HRP labeled nucleic acid complementary to sequences not normally found in specimens to be tested; and
(c) HRP labeled nucleic acid complementary to sequences normally found in specimens to be tested.

15. The kit of claim 14, wherein said horseradish peroxidase labeled nucleic acid comprises human papillomavirus nucleic acid.

* * * * *